(12) United States Patent
Kim

(10) Patent No.: US 12,053,191 B2
(45) Date of Patent: *Aug. 6, 2024

(54) DEVICE AND METHOD FOR TREATING OSTEONECROSIS

(71) Applicant: Texas Scottish Rite Hospital for Children, Dallas, TX (US)

(72) Inventor: Harry K. W. Kim, Dallas, TX (US)

(73) Assignee: Texas Scottish Rite Hospital for Children, Dallas, TX (US)

(*) Notice: Subject to any disclaimer, the term of this patent is extended or adjusted under 35 U.S.C. 154(b) by 847 days.

This patent is subject to a terminal disclaimer.

(21) Appl. No.: 16/945,270

(22) Filed: Jul. 31, 2020

(65) Prior Publication Data

US 2020/0360030 A1  Nov. 19, 2020

Related U.S. Application Data

(63) Continuation of application No. 15/490,595, filed on Apr. 18, 2017, now Pat. No. 10,758,253.

(51) Int. Cl.
*A61B 17/17*  (2006.01)
*A61B 17/16*  (2006.01)
(Continued)

(52) U.S. Cl.
CPC ...... *A61B 17/1764* (2013.01); *A61B 17/1617* (2013.01); *A61B 17/162* (2013.01);
(Continued)

(58) Field of Classification Search
CPC ............ A61B 17/1714; A61B 17/1725; A61B 17/1764; A61B 17/17; A61B 17/1644;
(Continued)

(56) References Cited

U.S. PATENT DOCUMENTS 5,437,683 A   8/1995  Neumann
5,772,661 A   6/1998  Michelson
(Continued)

OTHER PUBLICATIONS

Alves do Monte, F. et al. Development of a novel minimally invasive technique to washout necrotic bone marrow content from epiphyseal bone: A preliminary cadaveric bone study. Orthop Traumatol Surg Res 106, 709-715, doi:10.1016/j.otsr.2020.01.006 (2020).

(Continued)

*Primary Examiner* — Scott J Medway
*Assistant Examiner* — Anh Bui
(74) *Attorney, Agent, or Firm* — Edwin S. Flores; Daniel J. Chalker; Chalker Flores, LLP

(57) ABSTRACT

The present invention includes a method and devices for treating osteonecrosis in, e.g., children, adolescents, and adults comprising: identifying a subject in need of treatment for osteonecrosis; drilling two or more holes into a bone in need of treatment for osteonecrosis; inserting two or more needles or cannulas into the holes in the bone; washing an interior of the bone with a washing fluid introduced through one or more of the needles or cannulas inserted into the bone; and after washing the interior of the bone introducing one or more bone growth promoting materials or cells into the bone.

11 Claims, 7 Drawing Sheets

(51) Int. Cl.
  *A61B 17/34* (2006.01)
  *A61B 17/70* (2006.01)
  *A61B 17/88* (2006.01)

(52) U.S. Cl.
  CPC ...... *A61B 17/1628* (2013.01); *A61B 17/1675* (2013.01); *A61B 17/1682* (2013.01); *A61B 17/1684* (2013.01); *A61B 17/17* (2013.01); *A61B 17/1775* (2016.11); *A61B 17/1778* (2016.11); *A61B 17/3472* (2013.01); *A61B 17/7097* (2013.01); *A61B 17/1637* (2013.01); *A61B 2017/1651* (2013.01); *A61B 17/8805* (2013.01); *A61B 2217/005* (2013.01); *A61B 2217/007* (2013.01); *A61M 2210/02* (2013.01)

(58) Field of Classification Search
  CPC ............ A61B 17/1668; A61B 17/7097; A61B 17/8833; A61B 17/8805; A61B 17/3472; A61B 2217/005; A61B 2217/007
  See application file for complete search history.

(56) References Cited

U.S. PATENT DOCUMENTS

| | | | | |
|---|---|---|---|---|
| 5,897,317 | A | * | 4/1999 | Hansen ................. A61C 1/052 433/132 |
| 8,303,594 | B2 | | 11/2012 | Lynch et al. |
| 8,328,762 | B2 | | 12/2012 | Woehr |
| 9,138,317 | B2 | | 9/2015 | McGee |
| 9,550,010 | B2 | | 1/2017 | Schulz et al. |
| 10,758,253 | B2 | | 9/2020 | Kim |
| 10,765,453 | B2 | * | 9/2020 | Kim ................. A61B 17/1622 |
| 2003/0158553 | A1 | * | 8/2003 | Michelson ........... A61F 2/4611 606/915 |
| 2005/0177171 | A1 | | 8/2005 | Wetzler et al. |
| 2007/0055282 | A1 | * | 3/2007 | Muschler ............ A61B 10/025 606/92 |
| 2008/0103506 | A1 | * | 5/2008 | Volpi .................... A61B 17/88 606/96 |
| 2009/0326537 | A1 | * | 12/2009 | Anderson ............... A61B 17/17 606/80 |
| 2010/0191195 | A1 | | 7/2010 | Kirschenbaum |
| 2011/0087161 | A1 | | 4/2011 | Lidgren et al. |
| 2013/0066261 | A1 | | 3/2013 | Henniges et al. |
| 2013/0110112 | A1 | | 5/2013 | Yliopisto |
| 2014/0088551 | A1 | | 3/2014 | Vad et al. |
| 2015/0005777 | A1 | * | 1/2015 | Ferro ................. A61B 17/1624 606/85 |
| 2015/0044179 | A1 | | 2/2015 | Saeki |
| 2017/0197017 | A1 | | 7/2017 | Martin et al. |

OTHER PUBLICATIONS

Andreev, D. et al. Osteocyte necrosis triggers osteoclast-mediated bone loss through macrophage-inducible C-type lectin. J Clin Invest 130, 4811-4830, doi:10.1172/jci134214 (2020).

Aruwajoye, O. O., Monte, F., Kim, A. & Kim, H. K. W. A Comparison of Transphyseal Neck-Head Tunneling and Multiple Epiphyseal Drilling on Femoral Head Healing Following Ischemic Osteonecrosis: An Experimental Investigation in Immature Pigs. J Pediatr Orthop, doi:10.1097/BPO.0000000000001219 (2018).

Beltran, J. et al. Core decompression for avascular necrosis of the femoral head: correlation between long-term results and preoperative MR staging. Radiology 175, 533-536, doi:10.1148/radiology.175.2.2326478 (1990).

Bozic, K. J., Zurakowski, D. & Thornhill, T. S. Survivorship Analysis of Hips Treated with Core Decompression for Nontraumatic Osteonecrosis of the Femoral Head*. JBJS 81 (1999).

Cao, J. J. Effects of obesity on bone metabolism. Journal of Orthopaedic Surgery and Research 6, 30, doi:10.1186/1749-799X-6-30 (2011).

Carragee, E. J., Hurwitz, E. L. & Weiner, B. K. A critical review of recombinant human bone morphogenetic protein-2 trials in spinal surgery: emerging safety concerns and lessons learned. Spine Journal 11, 471-491, doi:10.1016/j.spinee.2011.04.023 (2011).

Carreira, A. C. et al. Bone Morphogenetic Proteins Facts, Challenges, and Future Perspectives. Journal of Dental Research 93, 335-345, doi:10.1177/0022034513518561 (2014).

Chen, N. F. et al. Symptomatic ectopic bone formation after off-label use of recombinant human bone morphogenetic protein-2 in transforaminal lumbar interbody fusion. J Neurosurg Spine 12, 40-46, doi:10.3171/2009.4.Spine0876 (2010).

Chughtai, M. et al. An evidence-based guide to the treatment of osteonecrosis of the femoral head. Bone Joint J 99-b, 1267-1279, doi:10.1302/0301-620x.99b10.Bjj-2017-0233.R2 (2017).

Deutsch, H. High-dose bone morphogenetic protein-induced ectopic abdomen bone growth. Spine J 10, e1-4, doi:10.1016/j.spinee.2009.10.016 (2010).

Fondi, C. & Franchi, A. Definition of bone necrosis by the pathologist. Clin Cases Miner Bone Metab 4, 21-26 (2007).

Garces, G. L., Mugica-Garay, I., Lopez-Gonzalez Coviella, N. & Guerado, E. Growth-plate modifications after drilling. J Pediatr Orthop 14, 225-228, doi:10.1097/01241398-199403000-00018 (1994).

Garrison, K. R. et al. Clinical effectiveness and cost-effectiveness of bone morphogenetic proteins in the non-healing of fractures and spinal fusion: a systematic review. Health Technol Assess 11, 1-150, iii-iv, doi:10.3310/hta11300 (2007).

Gerwin, N., Bendele, A. M., Glasson, S. & Carlson, C. S. The OARSI histopathology initiative—recommendations for histological assessments of osteoarthritis in the rat. Osteoarthritis Cartilage 18 Suppl 3, S24-34, doi:10.1016/j.joca.2010.05.030 (2010).

Henry Jay Forman, et al., What is the concentration of hydrogen peroxide in blood and plasma? Arch Biochem Biophys. Aug. 1, 2016;603:48-53. doi: 10.1016/j.abb.2016.05.005. Epub May 9, 2016. PMID: 27173735.

Herring, J. A., Kim, H. T. & Browne, R. Legg-Calve-Perthes disease. Part II: Prospective multicenter study of the effect of treatment on outcome. J Bone Joint Surg Am 86, 2121-2134 (2004).

Janarv, P. M., Wikstrom, B. & Hirsch, G. The influence of transphyseal drilling and tendon grafting on bone growth: an experimental study in the rabbit. J Pediatr Orthop 18, 149-154 (1998).

Kim, H. K. Pathophysiology and new strategies for the treatment of Legg-Calvé-Perthes disease. J Bone Joint Surg Am 94, 659-669, doi:10.2106/jbjs.J.01834 (2012).

Kim, H. K., et al., Local administration of bone morphogenetic protein-2 and bisphosphonate during non-weight-bearing treatment of ischemic osteonecrosis of the femoral head: an experimental investigation in immature pigs. J Bone Joint Surg Am 96, 1515-1524, doi:10.2106/jbjs.M.01361 (2014).

Kim, H. K. W. et al. Minimally Invasive Necrotic Bone Washing Improves Bone Healing After Femoral Head Ischemic Osteonecrosis: An Experimental Investigation in Immature Pigs. J Bone Joint Surg Am 103, 1193-1202, doi:10.2106/jbjs.20.00578 (2021).

Koob, T. J. et al. Biomechanical properties of bone and cartilage in growing femoral head following ischemic osteonecrosis. J Orthop Res 25, 750-757, doi:10.1002/jor.20350 (2007).

Li, Z. et al. Injectable gelatin derivative hydrogels with sustained vascular endothelial growth factor release for induced angiogenesis. Acta Biomater 13, 88-100, doi:10.1016/j.actbio.2014.11.002 (2015).

Lieberman, J. R., Conduah, A. & Urist, M. R. Treatment of osteonecrosis of the femoral head with core decompression and human bone morphogenetic protein. Clin Orthop Relat Res, 139-145, doi:10.1097/01.blo.0000150312.53937.6f (2004).

Liu, M. et al. Injectable hydrogels for cartilage and bone tissue engineering. Bone Res 5, 17014, doi:10.1038/boneres.2017.14 (2017).

Ma, C., Jing, Y., Sun, H. & Liu, X. Hierarchical Nanofibrous Microspheres with Controlled Growth Factor Delivery for Bone Regeneration. Adv Healthc Mater 4, 2699-2708, doi:10.1002/adhm.201500531 (2015).

Makela, E. A., Vainionpaa, S., Vihtonen, K., Mero, M. & Rokkanen, P. The effect of trauma to the lower femoral epiphyseal plate. An experimental study in rabbits. J Bone Joint Surg Br 70, 187-191, doi:10.1302/0301-620X.70B2.3346285 (1988).

(56) References Cited

OTHER PUBLICATIONS

Mcandrew, M. P. & Weinstein, S. L. A long-term follow-up of Legg-Calvé-Perthes disease. J Bone Joint Surg Am 66, 860-869, doi:10.2106/00004623-198466060-00006 (1984).

Molloy, M. K. & MacMahon, B. Incidence of Legg-Perthes disease (osteochondritis deformans). N Engl J Med 275, 988-990, doi:10.1056/NEJM196611032751804 (1966).

Mont, M. A., Carbone, J. J. & Fairbank, A. C. Core Decompression Versus Nonoperative Management for Osteonecrosis of the Hip. Clinical Orthopaedics and Related Research® 324 (1996).

Noemi Di Marzo, et al. The Role of Hydrogen Peroxide in Redox-Dependent Signaling: Homeostatic and Pathological Responses in Mammalian Cells. Cells. Oct. 4, 2018;7(10):156. doi: 10.3390/cells7100156. PMID: 30287799.

Ohta, H. et al. The effects of heat on the biological activity of recombinant human bone morphogenetic protein-2. J Bone Miner Metab 23, 420-425, doi:10.1007/s00774-005-0623-6 (2005).

Phipps, M. C., Monte, F., Mehta, M. & Kim, H. K. Intraosseous Delivery of Bone Morphogenic Protein-2 Using a Self-Assembling Peptide Hydrogel. Biomacromolecules 17, 2329-2336, doi:10.1021/acs.biomac.6b00101 (2016).

Quan Qing, et al., Effects of hydrogen peroxide on biological characteristics and osteoinductivity of decellularized and demineralized bone matrices, J Biomed Mater Res A. Jul. 2019;107(7):1476-1490. doi: 10.1002/jbm.a.36662. Epub Mar. 7, 2019. PMID: 30786151.

Ruppert, et al., Human bone morphogenetic protein 2 contains a heparin-binding site which modifies its biological activity. Eur J Biochem. Apr. 1, 1996;237(1):295-302. doi: 10.1111/j.1432-1033.1996.0295n.x. PMID: 8620887.

Schmidt, A., Schumacher, J. T., Reichelt, J., Hecht, H. J. & Bilitewski, U. Mechanistic and molecular investigations on stabilization of horseradish peroxidase C. Anal Chem 74, 3037-3045, doi:10.1021/ac0108111 (2002).

Shi, L., Sun, W., Gao, F., Cheng, L. & Li, Z. Heterotopic ossification related to the use of recombinant human BMP-2 in osteonecrosis of femoral head. Medicine (Baltimore) 96, e7413, doi:10.1097/md.0000000000007413 (2017).

Simmonds, M. C. et al. Safety and Effectiveness of Recombinant Human Bone Morphogenetic Protein-2 for Spinal Fusion A Meta-analysis of Individual-Participant Data. Annals of Internal Medicine 158, 877-+, doi:10.7326/0003-4819-158-12-201306180-00005 (2013).

Song, W. S., Yoo, J. J., Kim, Y. M. & Kim, H. J. Results of multiple drilling compared with those of conventional methods of core decompression. Clin Orthop Relat Res 454, 139-146, doi:10.1097/01.blo.0000229342.96103.73 (2007).

Stulberg, S. D., Cooperman, D. R. & Wallensten, R. The natural history of Legg-Calve-Perthes disease. J Bone Joint Surg Am 63, 1095-1108 (1981).

Sun, W. et al. Recombinant human bone morphogenetic protein-2 in debridement and impacted bone graft for the treatment of femoral head osteonecrosis. PLoS One 9, e100424, doi:10.1371/journal.pone.0100424 (2014).

Tsao, A. K. et al. Biomechanical and clinical evaluations of a porous tantalum implant for the treatment of early-stage osteonecrosis. J Bone Joint Surg Am 87 Suppl 2, 22-27, doi:10.2106/jbjs.E.00490 (2005).

Vandermeer, J. S. et al. Local administration of ibandronate and bone morphogenetic protein-2 after ischemic osteonecrosis of the immature femoral head: a combined therapy that stimulates bone formation and decreases femoral head deformity. J Bone Joint Surg Am 93, 905-913, doi:10.2106/jbjs.J.00716 (2011).

Weinstein, R. S. Glucocorticoid-induced osteonecrosis. Endocrine 41, 183-190, doi:10.1007/s12020-011-9580-0 (2012).

Weinstein, S. L. Bristol-Myers Squibb/Zimmer award for distinguished achievement in orthopaedic research. Long-term follow-up of pediatric orthopaedic conditions. Natural history and outcomes of treatment. J Bone Joint Surg Am 82-a, 980-990, doi:10.2106/00004623-200007000-00010 (2000).

Wong, D. A., Kumar, A., Jatana, S., Ghiselli, G. & Wong, K. Neurologic impairment from ectopic bone in the lumbar canal: a potential complication of off-label PLIF/TLIF use of bone morphogenetic protein-2 (BMP-2). Spine J 8, 1011-1018, doi:10.1016/j.spinee.2007.06.014 (2008).

Zhang, Y. et al. A new 3D printed titanium metal trabecular bone reconstruction system for early osteonecrosis of the femoral head. Medicine (Baltimore) 97, e11088, doi:10.1097/md.0000000000011088 (2018).

Zhao, D. et al. Guidelines for clinical diagnosis and treatment of osteonecrosis of the femoral head in adults (2019 version). J Orthop Translat 21, 100-110, doi:10.1016/j.jot.2019.12.004 (2020).

Joseph, B., Mulpuri, K. & Varghese, G. Perthes' disease in the adolescent. The Journal of bone and joint surgery. British vol. 83, 715-720, doi: 10.1302/0301-620x.83b5.10663 (2001).

International Search Report and Written Opinion of USPTO for PCT/US2018/028137 dated August 9, 2018, 15 pp.

\* cited by examiner

Unwashed
Washed
4x
10x
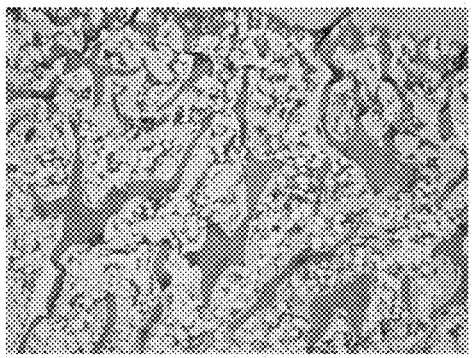
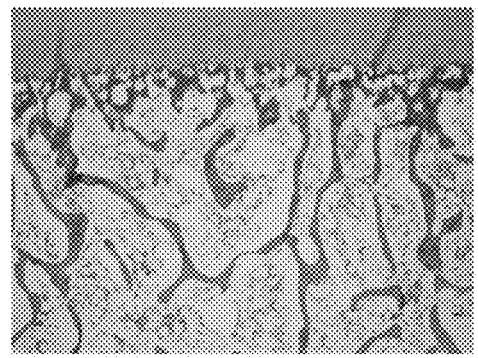
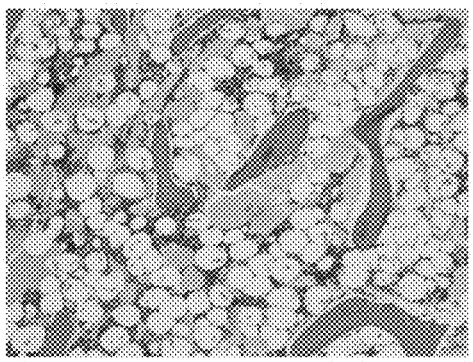
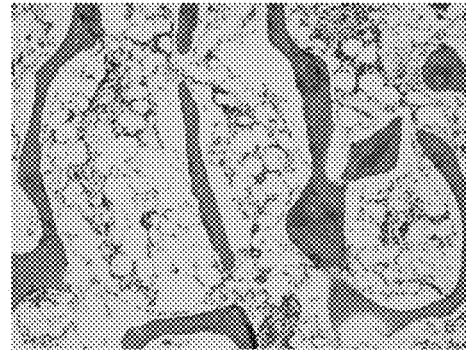
FIG. 6A
FIG. 6B
Control
No wash
Saline Wash
(180 ml)
Ethanol 100% (60 ml) +
Saline 120 ml Wash
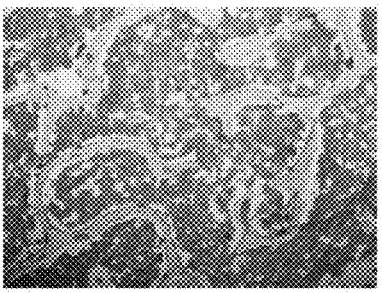
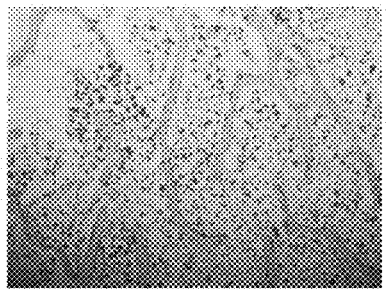
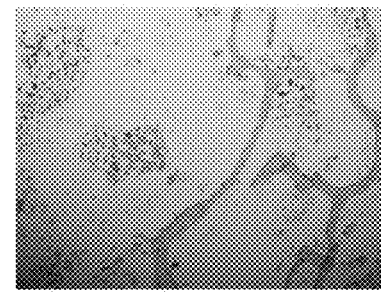
FIG. 7A
FIG. 7B
FIG. 7C Single Needle
No wash Four Needles
Washed

DEVICE AND METHOD FOR TREATING OSTEONECROSIS

CROSS-REFERENCE TO RELATED APPLICATIONS

This application is a continuation application of U.S. patent application Ser. No. 15/490,595 filed on Apr. 18, 2017 and entitled "Device and Method for Treating Osteonecrosis," the contents of which are incorporated by reference in their entirety.

This application is related to U.S. patent application Ser. No. 16/936,084 filed Jul. 22, 2020 and entitled "Device and Method for Treating Osteonecrosis," which is a continuation application of U.S. patent application Ser. No. 15/956,245 filed on Apr. 18, 2018, which is a continuation-in-part application of U.S. patent application Ser. No. 15/490,595 filed on Apr. 18, 2017.

STATEMENT OF FEDERALLY FUNDED RESEARCH

None.

TECHNICAL FIELD OF THE INVENTION

The present invention relates in general to the field of osteonecrosis, and more particularly, to a novel device and method for treating osteonecrosis, such as, Legg-Calve-Perthes disease.

BACKGROUND OF THE INVENTION

Without limiting the scope of the invention, its background is described in connection with tissue regeneration.

One such method is taught in U.S. Pat. No. 9,138,317, issued to McGee, entitled "Conduits for enhancing tissue regeneration", which is said to teach apparatuses, systems, and methods for enhancing bone or soft tissue regeneration. For example, a conduit, having one or more segments, can originate at a tissue regeneration site and can have a first opening to promote physiological signals to enter the conduit and transit to a second opening that penetrates a histologically rich source of multipotent mesenchymal cells, promoting the multipotent mesenchymal cells to produce a tissue regeneration response products, the response products transiting through the second opening to egress at the first opening of the conduit, and promoting tissue regeneration at the tissue regeneration site.

Another such method is taught in U.S. Pat. No. 8,382,762, issued to Brannon, entitled "Endoscopic bone debridement", which is said to teach an osteoendoscopic cylinder for tamponading bleeding along a longitudinal canal surface of an osteocentral canal of a femoral neck so as to allow endoscopic visualization of a segment of osteonecrotic bone within a femoral head. The osteoendoscopic cylinder is of a dimension adapted to receive an endoscope therein and includes an inner visual surface and an outer bony contact surface. An orientation mark along the inner visual surface is of a size and dimension to ensure a first visualization thereof with the endoscope.

SUMMARY OF THE INVENTION

In one embodiment, the present invention includes a method of treating osteonecrosis comprising: identifying a subject in need of treatment for osteonecrosis; drilling two or more holes into a bone in need of treatment for osteonecrosis; inserting two or more needles or cannulas into the holes in the bone; washing an interior of the bone with a washing fluid introduced through one or more of the needles or cannulas inserted into the bone; and after washing the interior of the bone introducing one or more bone growth promoting materials into the bone. In one aspect, the washing fluid is a biocompatible isotonic fluid and optionally comprises biocompatible detergents, biocompatible surfactants, biocompatible alcohols, antibiotics, preservatives, or combinations thereof. In another aspect, the method further comprises injecting the washed bone with at least one of autologous bone marrow, autologous bone stem cells, bone growth material, bone graft material, bone void filler, cancellous bone graft or fragments, hydrogels, gelatins, osteoconductive material, osteoproliferative material, osteoinductive material, a bone morphogenic cytokine, bone morphogenic protein, a bone morphogenic protein-2 (BMP-2), bone material infused collagen matrix, or bone morphogenic protein infused collagen matrix. In another aspect, the method further comprises washing the interior of the bone until the washing fluid is clear. In another aspect, the bone is a femoral head, a humeral head, a knee condyle, or an ankle talus. In another aspect, the washing fluid cleans at least 50, 60, 70, 75, 80, 85, or 90% of the volume within the bone. In another aspect, the method further comprises measuring the amount of cell debris and fat in the washing fluid and washing until the amount of cell debris and fat in the washing fluid is minimized. In another aspect, the method further comprises injecting the washing fluid through a first needle or cannula and drawing the washing fluid out of a second needle or cannula. In another aspect, the surgical instrument further comprises washing fluid is introduced and drawn with a syringe attached to the needle or cannula.

In another embodiment, the present invention includes a method of treating Legg-Calvé-Perthes Disease comprising: identifying a subject in need of treatment for Legg-Calvé-Perthes Disease; drilling two or more holes into a femoral head; inserting two or more needles or cannulas into the femoral head; washing an interior of the femoral head with a washing fluid introduced through one or more of the needles or cannulas drilled into the femoral head; and after washing the interior of the femoral head introducing a bone growth promoting material into the femoral head. In one aspect, the method further comprises washing fluid is a biocompatible isotonic fluid and optionally comprises biocompatible detergents, biocompatible surfactants, biocompatible alcohols, antibiotics, preservatives, or combinations thereof. In another aspect, the subject is a pediatric, an adolescent, or an adult. In another aspect, the femoral head osteonecrosis is idiopathic (unknown cause) or due to corticosteroid, trauma, alcohol, sickle cell disease, or other known causes of osteonecrosis. In another aspect, the method further comprises injecting the washed bone with at least one of autologous bone marrow, autologous bone stem cells, bone growth material, bone graft material, bone void filler, cancellous bone graft or fragments, hydrogels, gelatins, osteoconductive material, osteoproliferative material, osteoinductive material, a bone morphogenic cytokine, bone morphogenic protein, a bone morphogenic protein-2 (BMP-2), bone material infused collagen matrix, or bone morphogenic protein infused collagen matrix. In another aspect, the method further comprises washing the interior of the femoral head until the washing fluid is clear before injecting the bone growth promoting material into the femoral head. In another aspect, the washing fluid cleans at least 50, 60, 70, 75, 80, 85, or 90% of the volume within the femoral head.

In another aspect, the method further comprises measuring the amount of cell debris and fat in the washing fluid and washing until the amount of cell debris and fat in the washing fluid is minimized. In another aspect, the method further comprises washing fluid through a first needle or cannula and drawing the washing fluid out of a second needle or cannula. In another aspect, the washing fluid is introduced into the femoral head and drawn from the femoral head with a syringe attached to the needle or cannula.

Yet another embodiment of the present invention includes a surgical instrument comprising: a first and a second drill bit capable of drilling into a femoral head, a humeral head, a knee condyle, or an ankle talus, wherein the first and second drills create adjacent holes in the femoral head, the humeral head, the knee condyle, or the ankle talus; one or more motors attached to and capable of rotating the first and second drill bits; a handle to control the direction of the first and second drill bits; and an on/off switch connected to the motor. In one aspect, at least one of the drill bits is defined further as a needle or cannula. In another aspect, the one or more motors are electrical, mechanical, pneumatic, hydraulic, or combinations thereof. In another aspect, the surgical instrument further comprises one or more gears between the one or more motors and the two or more drills that at least one of: increase or decrease the speed of the two or more drills, or increase or decrease the torque of the two or more drills. In another aspect, the apparatus further comprises one or more drill chucks capable of holding drills of different sizes. In another aspect, the on/off switch is a variable speed switch. In another aspect, the apparatus further comprises a cam that provides a hammer action, a rotary action, or both a rotary and hammer action, to the two or more drill bits. In another aspect, the drill bits or the apparatus is disposable. In another aspect, the subject is a pediatric, an adolescent, or an adult. In another aspect, the femoral head osteonecrosis is idiopathic (unknown cause) or due to corticosteroid, trauma, alcohol, sickle cell disease, or other known causes of osteonecrosis. In another aspect, the surgical instrument further comprises a drill press mechanism at least one of: increases the control by a user, increases a leverage of a user, or is adjustable to increase or decrease an angle between the two or more drill bits to compensate for the size of the femoral head, wherein the drill press is angled to direct the two or more drill bits into a region at or below the greater trochanter or humerus metaphysis, through a neck of the femur or humerus, and into the femoral or humeral head. In another aspect, the surgical instrument further comprises one or more sleeves or tubes surrounding the two or more drill bits, wherein the sleeves are adapted to remain after the drills have been removed from the femoral head to at least one of: facilitate the washing of the femoral head, or introduce bone growth promoting agents into the femoral head. In another aspect, the one or more drill bits are internally cooled. In another aspect, the one or more drill bits comprise a slow spiral, a standard spiral, a quick spiral, a worm spiral, two or more flutings, a split point, or a step tip. In another aspect, the surgical instrument further comprises a drill guide that controls the direction of the two or more drill bits, wherein the drill guide is adapted to be affixed to a skin adjacent the femoral head, wherein openings in the drill guide are aligned with a greater trochanter, a neck of the femur, and the femoral head.

In yet another embodiment, the present invention includes a drill guide that controls the direction of the two or more drill bits, comprising: two or openings in the drill guide are aligned with a greater trochanter, a neck of the femur, and the femoral head; and a skin attachment mechanism, wherein the skin attachment mechanism affixes, at least temporarily, the drill guide in communication with the greater trochanter, the neck of the femur, and the femoral head. In one aspect, the skin attachment mechanism is an adhesive, a pin or pins, and/or one or more suction cups. In another aspect, the skin attachment mechanism is an arm of an apparatus controllable in an x-y, a y-z, an x-z, or an x-y-z axis.

BRIEF DESCRIPTION OF THE DRAWINGS

For a more complete understanding of the features and advantages of the present invention, reference is now made to the detailed description of the invention along with the accompanying figures and in which:

FIGS. 6A and 6B each show the histology at a low (4×) and a high (10×) magnification of the unwashed femoral head (FIG. 6A) and the washed femoral head (FIG. 6B) according to the present invention.

FIGS. 7A to 7C show the histology of the femoral head without (FIG. 7A), with a saline wash (FIG. 7B) and with an ethanol and saline wash (FIG. 7C) to remove fat and cell debris.

DETAILED DESCRIPTION OF THE INVENTION

Figure 1A:
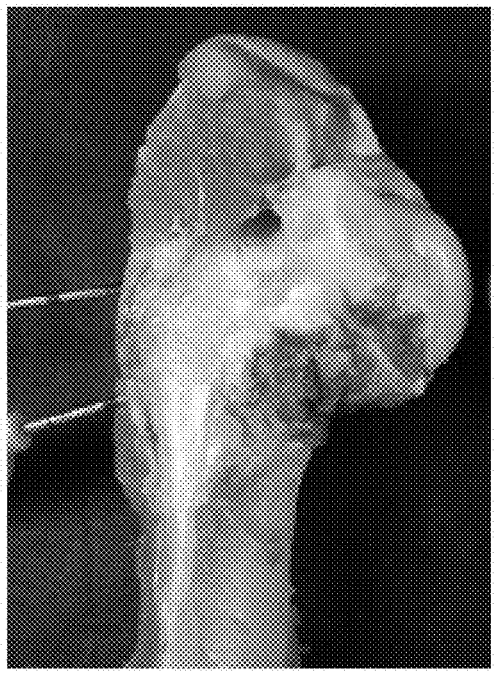
FIGS. 1A and 1B show a photograph (FIG. 1A) and a matching radiograph (FIG. 1B) of a humeral head into which two needles or cannulas are inserted of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

New Necrotic Bone Washing Technique

The bone washing technique of the present invention involves placement of two or more intra-osseous needles or cannulas into pediatric or adult femoral heads for treatment of avascular necrosis (AVN) or osteonecrosis. This technique permits inflow and outflow of washing solution through the needle(s) or cannula(s) to remove, e.g., dead cell debris, necrotic marrow fat, and/or inflammatory factors. It is demonstrated herein that the removal of dead cell debris, necrotic marrow fat, and/or inflammatory factors from the marrow space significantly improves bone healing and creates space for the injection or infusion of biological therapeutic agents and/or stem cells.

Briefly, two or more intra-osseous needles and/or cannulas are placed 5-15 mm apart depending on the necrotic bone volume and the size of the femoral head. Either transarticular (through the joint and articular cartilage) or transphyseal/metaphyseal (starting from region below the greater trochanter) or combination needle placement technique can be used. The needles are most often inserted under fluoroscopic guidance and a specialized needle placement device may be used to facilitate the placement of the needles. The present invention can be used in a wide variety of locations that includes osteonecrosis, e.g., the femoral head, the humeral head, the knee condyle, or the ankle talus.

After the placement of two or more intra-osseous needles and/or cannulas within the necrotic bone, aspiration (negative pressure), injection/infusion (positive pressure), and/or a combination of both, are used to provide a high volume of washing solution to flow through the necrotic femoral head to remove the dead cell debris. A high volume washing of the necrotic bone can be facilitated by using a mechanical device or a pump. The amount of volume required for washing or the termination of the washing technique can be determined by assessing the clarity/turbidity of the outflow solution. Further assessment of the outflow solution can be done by measuring levels of specific inflammatory factors using visual, qualitative and/or quantitative assays.

The needles and/or cannulas will generally have following specifications: (1) 6, 7, 8, 9, 10, 11, 12, 13, 14, 15, or 6-15 gauge in diameter, depending on the size of the femoral head and the bone necrosis; (2) the tip of the needle should be less than 1.5 mm long to avoid unintentional penetration through the femoral head, but can be 8, 9, 10, 12, 15, 20, 25, 30 or more centimeters, e.g., 10 to 30 cm; and/or (3) the needle may have one or more fenestrations near the tip to increase the distribution and collection of bone washing solution.

A wide variety of washing solutions and combinations of solutions are contemplated for use with the present invention. The washing solution can be based on saline, various concentrations of ethanol, and/or include one or more biocompatible detergent and/or surfactants for removing/extracting cell debris, necrotic fat, or the necrotic extracellular matrix. The washing solution may also include antibiotics or other antimicrobial agents. The washing solution may also contain one or more bioactive agents, enzymes, or nanoparticles that facilitate the removal of the necrotic fat and the extracellular matrix in the necrotic bone marrow. The washing solution may also contain drugs or agents that stimulate angiogenesis (for instance by activation of hypoxia inducible factor-1 and vascular endothelial growth factor pathways) or stimulate osteogenesis (for instance through Wnt and/or BMP signaling pathways).

Generally, the temperature of wash solution should be warmed up to the body temperature to be physiological and more effective in removing cell debris.

Example 2

New Stem Cell or Bone Active Agent Delivery Technique

The bone delivery technique involves placement of two or more intra-osseous needles and/or cannulas into pediatric or adult femoral heads for treatment of avascular necrosis (AVN) or osteonecrosis. This technique can be used with or without first performing the bone washing technique outlined above. The use of two or more intra-osseous delivery needles and/or cannulas improves the local distribution of stem cells or bone active agents in the necrotic femoral head by subdividing the total volume of cells or bone active agents to be injected into multiple sites. The technique also improves the local retention of stem cells or bone active agents by decreasing the backflow pressure, unlike the single needle delivery technique where the total volume of injectant is delivered through a single needle site.

This technique can be used to inject cells or bone active agents alone or in combination with a delivery/carrier agent such as hydrogel or gelatin, which can be chemically designed to improve the retention of stem cells and growth factors such as bone morphogenetic proteins (BMPs).

The use of two or more needles and/or cannulas also permits two-step preparation of the necrotic bone for the delivery of stem cells or bone active agents. In the first step, a bone washing and preparation solution will be used to remove the cell debris and to distribute a chemical or catalyst required for a chemical reaction which will improve the local retention of a delivery agent and a growth factor when they are injected or infused in the second step.

The needle and/or cannulas specification are same as that for the bone washing technique described above.

Figure 1B:

FIGS. 1A and 1B show a photograph (FIG. 1A) and a matching radiograph (FIG. 1B) of a humeral head into which two needles (Vidacare, San Antonio, Texas) or cannulas are inserted of the present invention in a model pig humeral head. The present invention allows the user to either inject and/or aspirate or both (i.e. positive and/or negative pressure washing), decreases the pressure of injection associated with single needle technique, and minimizes leakage. In the prior art using the single needle technique it is known that the leakage of bone promoting factors, such as BMP-2 leads to the formation of bone outside the femoral head as a result of leakage, which greatly increases the morbidity of the procedure. The present invention eliminates leakage and the growth of bone outside the femoral head. In particular, a material that is sufficiently viscous is injected/aspired that prohibits its release outside the femoral head, and/or plugs (e.g., biodegradable plugs) can be inserted into the openings to prevent leakage.

Figure 2:
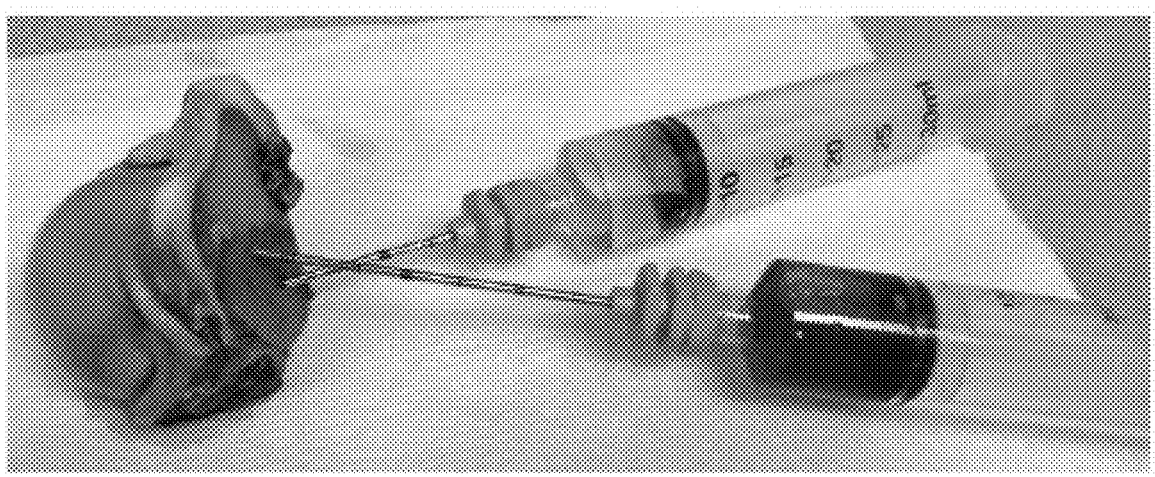
FIG. 2 shows a femoral head into which two needles or cannulas are inserted and are connected to syringes, the top syringe having a clear washing fluid, and the bottom syringe showing cell debris and fat in the washing fluid after traversing the femoral head.

FIG. 2 shows a femoral head of a pig into which two needles or cannulas are inserted and are connected to syringes, the top syringe having a clear washing fluid, and the bottom syringe showing cell debris and fat in the washing fluid after traversing the femoral head. By washing out necrotic bone to remove necrotic cell debris and inflammatory factors the present invention improve bone healing.

Figure 3A:
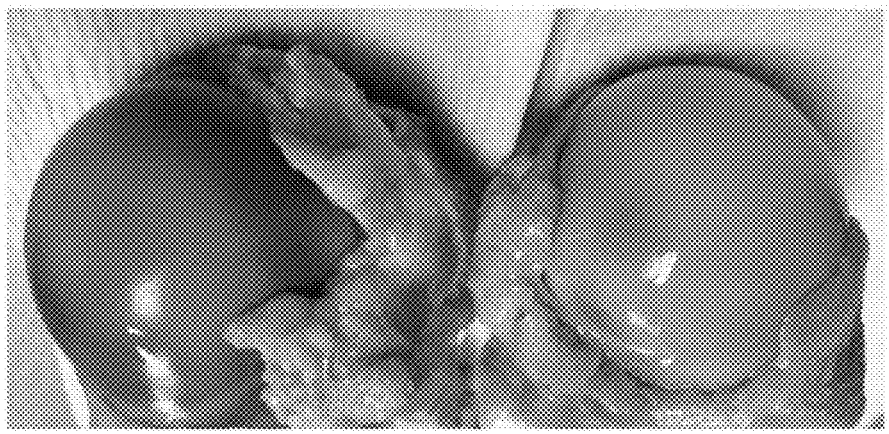
FIG. 3A shows on the left an unwashed femoral head, and the right a washed femoral head using the present invention.
Figure 3B:
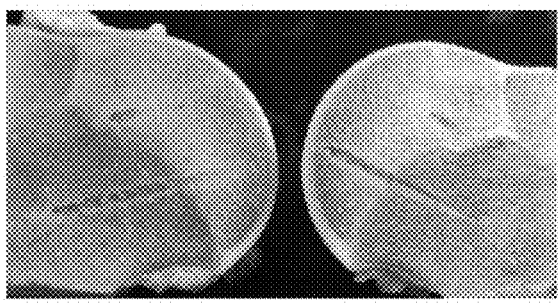
FIG. 3B shows a cross-section of an unwashed femoral head.
Figure 3C:
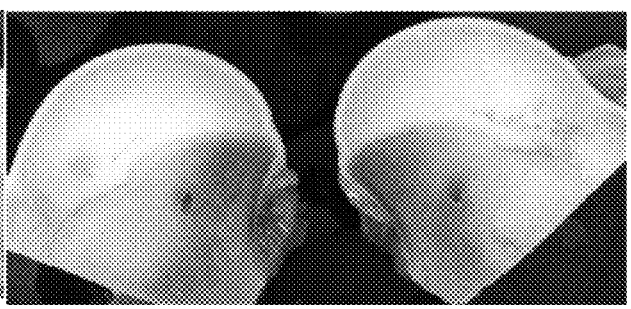
FIG. 3C shows a cross-section of a femoral head washed according to the present invention.
Figure 4:
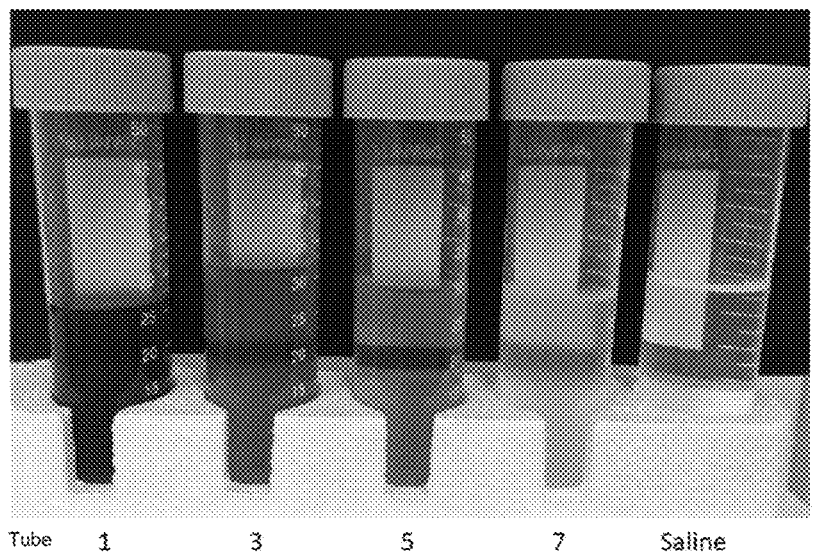
FIG. 4 shows a progression of washes of the femoral head shows in FIG. 3C and on the right the initial saline.

FIG. 3A shows on the left an unwashed femoral head of a pig, and the right a washed femoral head using the present invention. FIG. 3B shows a cross-section of an unwashed femoral head of a pig. FIG. 3C shows a cross-section of a femoral head of a pig washed according to the present invention. FIG. 4 shows a progression of washes of the femoral head of a pig shows in FIG. 3C and on the right the initial saline, which demonstrates the removal of dead cell debris, necrotic marrow fat, and/or inflammatory factors.

Figure 5A:
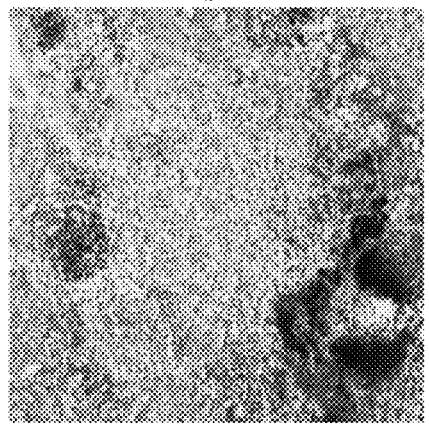
FIGS. 5A and 5B show a low and a high magnification, respectively, of the wash solution after cyto-spin to demonstrate that the solution contains cell debris from the femoral head.
Figure 5B:
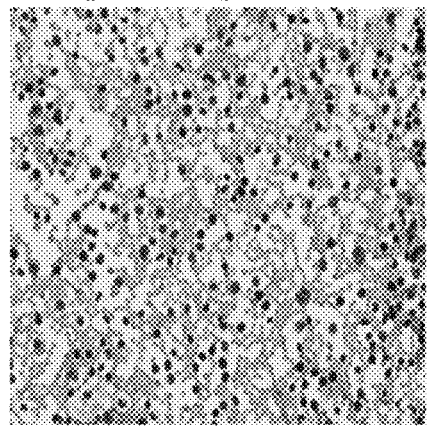

FIGS. 5A and 5B show a low and a high magnification, respectively, of the wash solution after cyto-spin to demonstrate that the solution contains cell debris from the femoral head of a pig. The wash solution was shown to contain cell debris that was washed out of the femoral head.

FIGS. 6A and 6B each show the histology at a low (4×) and a high (10×) magnification of the unwashed femoral head (FIG. 6A) and the washed femoral head (FIG. 6B) according to the present invention.

FIGS. 7A to 7C show the histology of the femoral head without (FIG. 7A), with a saline wash (FIG. 7B) and with an ethanol and saline wash (FIG. 7C) to remove fat and cell debris. It was found that saline wash removes fat and cell debris, while ethanol further removes fat. Both wash solutions were shown to create space for bone stimulating biomaterials including marrow stem cells.

Figure 8A:
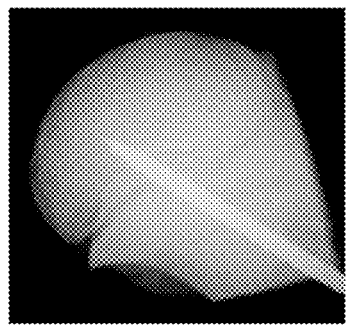
FIG. 8A shows a single needle of the prior art (left, radiograph), and the distribution of an imaging agent injected into the femoral head (right) through the single opening.
Figure 8A:
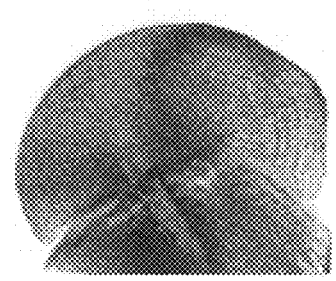
Figure 8B:
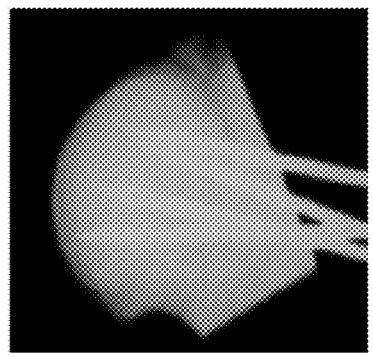
FIG. 8B shows a multiple needle (left, radiograph), wash, and injection of the distribution of an agent injected into the femoral head (right) using a four opening method in which one or two needles or cannulas are used to wash and two or three needles used to remove the wash and, likewise, the delivery the imaging agent using the present invention.
Figure 8B:
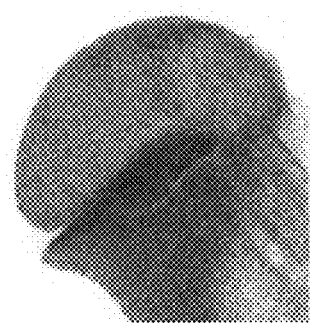

FIG. 8A shows a single needle of the prior art (left, radiograph), and the distribution of an imaging agent injected into the femoral head (right) through the single opening. FIG. 8B shows a multiple needle (left, radiograph), wash, and injection of the distribution of an agent injected into the femoral head (right) using a four opening method in which one or two needles or cannulas are used to wash and two or three needles used to remove the wash and, likewise, the delivery the imaging agent using the present invention. The images on the right clearly show that the multiple needle/cannula method provides a much wider distribution of the visualization agent, while the single injection shows an umbrella-like distribution.

Figure 9:
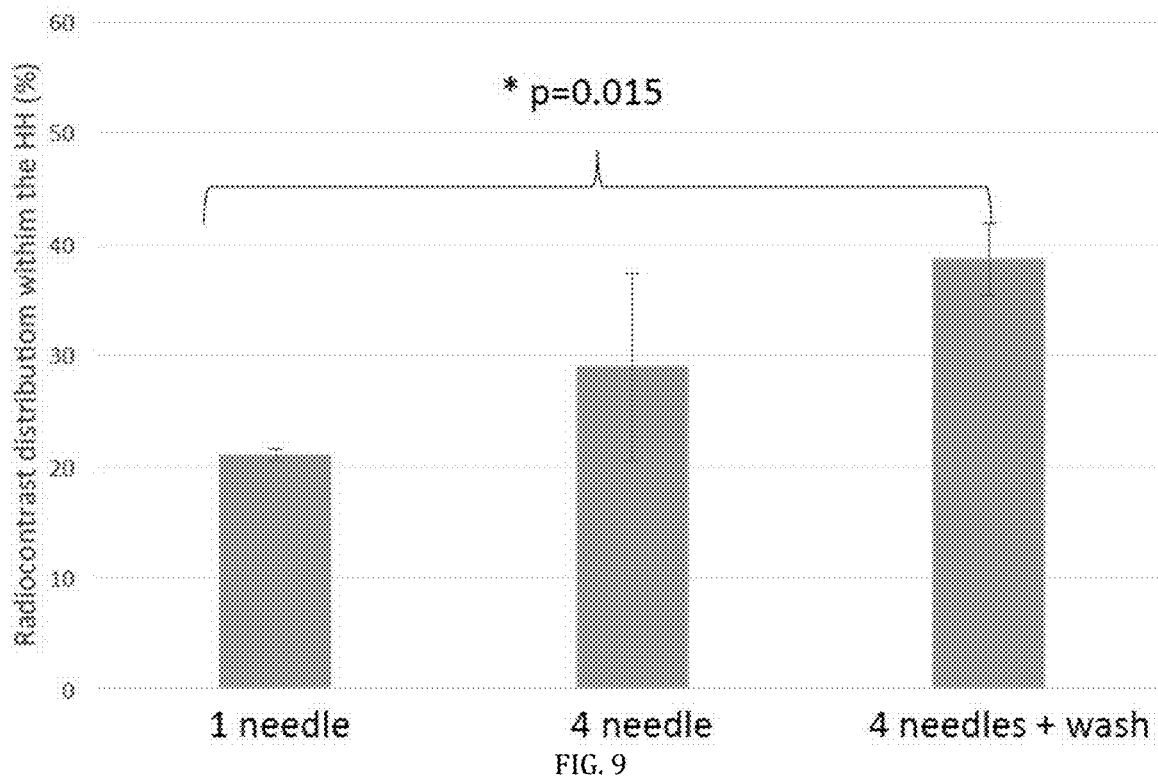
FIG. 9 is a graph that compares the prior art with a 4 needle/cannula method, and the 4 needle/cannula method that also included the wash, and the distribution of the imaging agent in the femoral head.

FIG. 9 is a graph that compares the prior art with a 4 needle/cannula method, and the 4 needle/cannula method that also included the wash, and the distribution of the imaging agent in the femoral head.

Figures 10A, 10B, 10C:
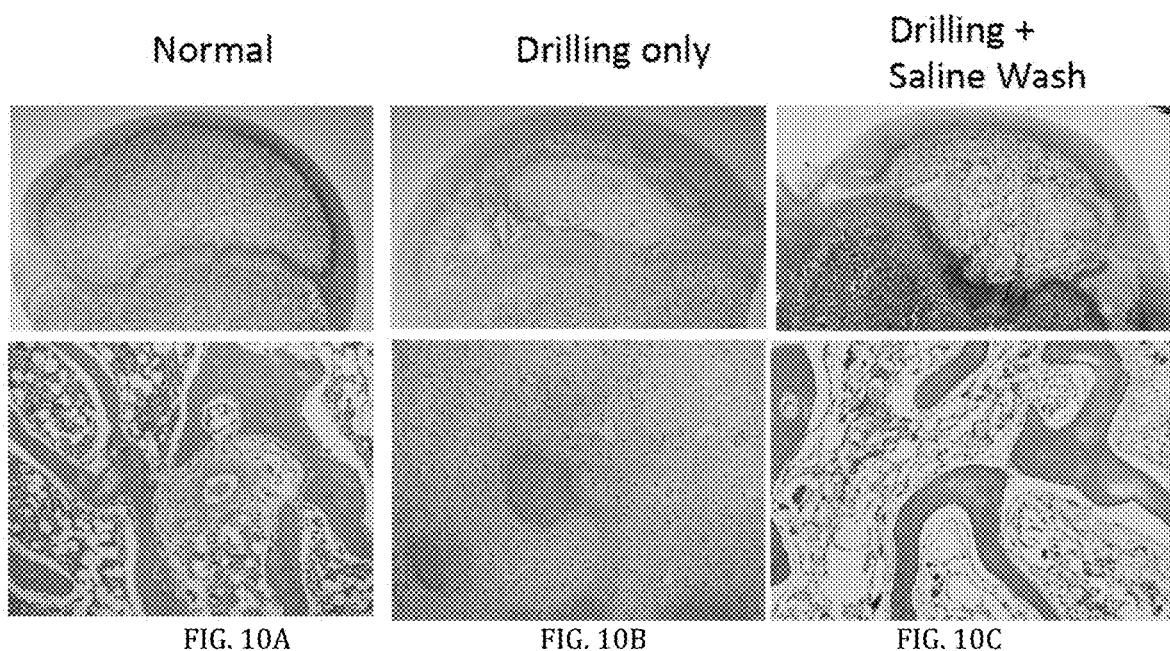
FIGS. 10A to 10C shows the histology of the femoral head of a normal femoral head (FIG. 10A), after multiple drilling only (FIG. 10B) and multiple drilling and saline wash (FIG. 10C), wherein bone washing improved bone healing, showed decreases resorption and increased bone formation.

FIGS. 10A to 10C show the histology of the femoral head of a normal femoral head (FIG. 10A), after drilling only (FIG. 10B) and drilling and saline wash (FIG. 10C), wherein bone washing improved bone healing, showed decreases resorption and increased bone formation. Thus, the bone washing of the present invention improves bone healing, shows decreased resorption, and increased bone formation.

Figure 11A:
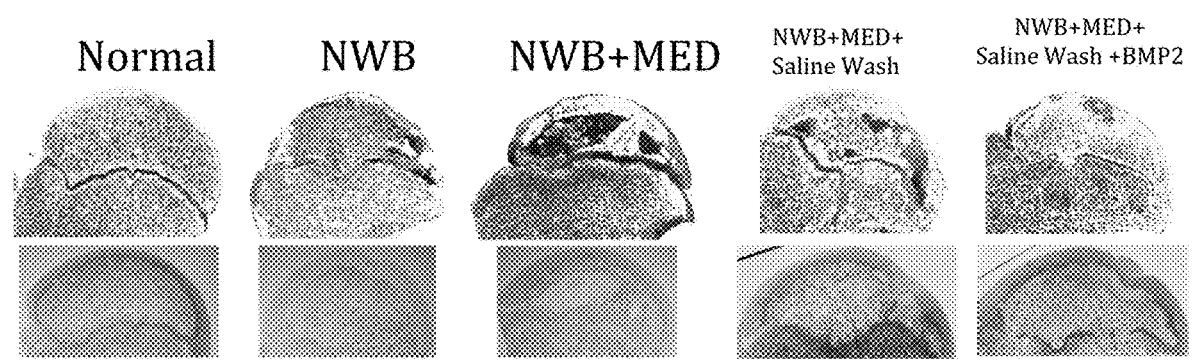
FIG. 11A shows micro-computer tomography (Micro-CT) and histologic assessments comparing a normal femoral head, a femoral head treated with the non-weight bearing method of the prior art, the non-weight bearing and multiple drilling of the prior art, non-weight bearing+multiple drilling+saline wash of the present invention, and non-weight bearing+multiple drilling+saline wash+BMP2/gelatin injection of the present invention.
Figure 11B:
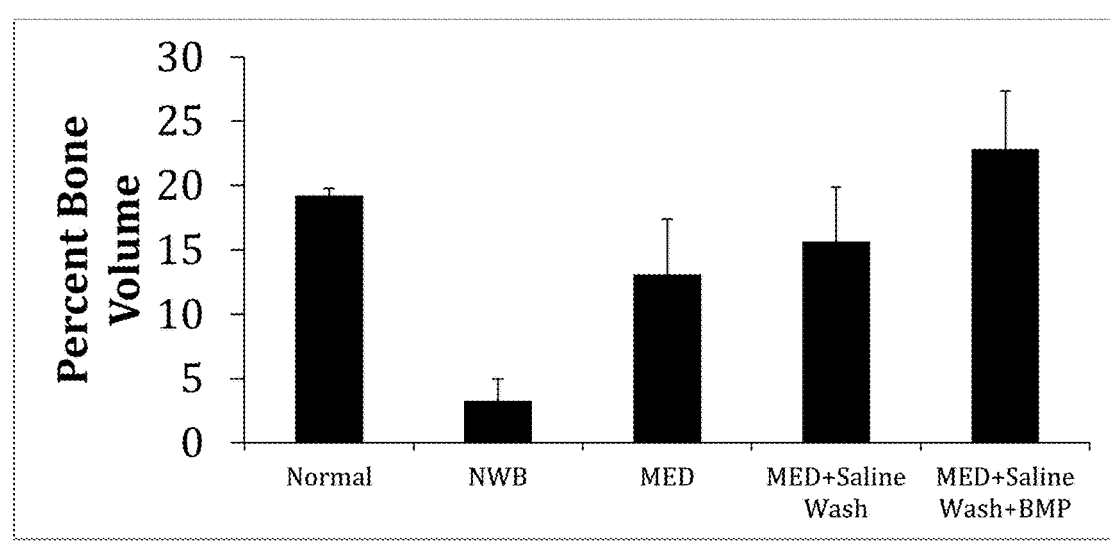
FIG. 11B is a graph that compares a percent bone volume of a normal femoral head, a femoral head treated with the non-weight bearing method of the prior art, the non-weight bearing and multiple drilling of the prior art, non-weight bearing+multiple drilling+saline wash of the present invention, and non-weight bearing+multiple drilling+saline wash+BMP2/gelatin injection of the present invention.

FIG. 11A shows a micro-computer tomography (Micro-CT) assessment compares a normal femoral head, a femoral head treated with the non-weight bearing method of the prior art, the non-weight bearing and multiple drilling of the prior art, and non-weight bearing+drilling,+saline wash of the present invention. FIG. 11B is a graph that compares a percent bone volume of a normal femoral head, a femoral head treated with the non-weight bearing method of the prior art, the non-weight bearing and multiple drilling of the prior art, and non-weight bearing+multiple drilling,+saline wash of the present invention.

In conclusion, the present invention includes: (1) the development of a minimally invasive method to wash out dead cells and necrotic fat materials from the marrow to improve bone healing, (2) the ability to lower the pressure of injection and minimize leakage of therapeutic agents, and (3) the ability to increase the distribution of therapeutic agents.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A surgical instrument comprising:
   a first and a second drill bit, needle or cannula, capable of drilling into a bone to form a first and a second hole in the bone;
   one or more motors attached to and capable of rotating the first and second drill bits;
   a cam that provides a hammer action, a rotary action, or both a rotary and hammer action, to the first and second drill bits;
   a handle to control the direction of the first and second drill bits; and
   an on/off switch connected to the one or more motors; and
   a first sleeve and a second sleeve surrounding the first and second drill bits, respectively,
   wherein the first sleeve and the second sleeve are adapted to remain after the first and second drill bits have been removed from the bone, and
   wherein first sleeve and a second sleeve are configured to introduce a washing fluid into an interior of the bone through the first hole in the bone until the washing fluid collected from the second hole is free of at least one of dead cell debris, necrotic marrow fat, or inflammatory factors, such that after washing the interior of the bone, either the first, the second, or both the first and second openings can be used to introduce one or more bone growth promoting agents into the bone.

2. The surgical instrument of claim 1, wherein at least one of the first and second drill bits is defined further as a needle or cannula.

3. The surgical instrument of claim 2, wherein the needle or cannula with an opening on the tip or side of the needle or cannula increases distribution and collection of a washing fluid or increases distribution of one or more injectants such as stem cells and bioactive materials and proteins.

4. The surgical instrument of claim 1, wherein the one or more motors are electrical, mechanical, pneumatic, hydraulic, or combinations thereof.

5. The surgical instrument of claim 1, further comprising one or more gears between the one or more motors and the first and second drill bits that increase or decrease the speed of the two or more drills, increase or decrease the torque of the two or more drills, or both.

6. The surgical instrument of claim 1, further comprising one or more drill chucks capable of holding drills of different sizes.

7. The surgical instrument of claim 1, wherein the first and second drill bits or the surgical instrument is disposable.

8. The surgical instrument of claim 1, further comprising a drill press mechanism that increases the control by a user, increases a leverage of a user, or is adjustable to increase or decrease an angle between the two or more drill bits to compensate for the size of the femoral head, or some combination;
   wherein the drill press mechanism is angled to direct the first and second drill bits into a region at or below the greater trochanter or humerus metaphysis, through a neck of the femur or humerus, and into the femoral or humeral head.

9. The surgical instrument of claim 1, wherein the first and second drill bits are internally cooled.

10. The surgical instrument of claim 1, wherein the first and second drill bits comprise a slow spiral, a standard spiral, a quick spiral, a worm spiral, two or more flutings, a split point, or a step tip.

11. The surgical instrument of claim 1, further comprising a drill guide that controls the direction of the first and second drill bits, wherein the drill guide is adapted to be affixed to a skin adjacent the femoral head, wherein openings in the drill guide are aligned with a greater trochanter, a neck of the femur, and the femoral head.

* * * * *